United States Patent
Jeong et al.

(10) Patent No.: US 12,329,819 B2
(45) Date of Patent: Jun. 17, 2025

(54) METHOD FOR MANUFACTURING NUCLEIC ACID FILM AND APPARATUS FOR INJECTING MEDICINE USING NUCLEIC ACID FILM

(71) Applicant: Korea Institute of Machinery & Materials, Daejeon (KR)

(72) Inventors: Jun-ho Jeong, Daejeon (KR); Yun Woo Lee, Daejeon (KR); So Hee Jeon, Seoul (KR); Junhyuk Choi, Daejeon (KR); Dae-Guen Choi, Sejong-si (KR); Ji Hye Lee, Daejeon (KR); Joo Yun Jung, Daejeon (KR)

(73) Assignee: Korea Institute of Machinery & Materials, Daejeon (KR)

(*) Notice: Subject to any disclaimer, the term of this patent is extended or adjusted under 35 U.S.C. 154(b) by 922 days.

(21) Appl. No.: 17/322,942

(22) Filed: May 18, 2021

(65) Prior Publication Data

US 2021/0268111 A1    Sep. 2, 2021

Related U.S. Application Data

(62) Division of application No. 16/091,521, filed as application No. PCT/KR2017/004084 on Apr. 14, 2017, now Pat. No. 11,040,103.

(30) Foreign Application Priority Data

Apr. 15, 2016  (KR) .................. 10-2016-0046275
Sep. 12, 2016  (KR) .................. 10-2016-0117332

(51) Int. Cl.
*A61K 47/26*    (2006.01)
*A61K 9/00*     (2006.01)
(Continued)

(52) U.S. Cl.
CPC .............. *A61K 47/26* (2013.01); *A61K 9/00* (2013.01); *A61K 9/0021* (2013.01); *A61K 9/70* (2013.01);
(Continued)

(58) Field of Classification Search
CPC ........ A61K 47/26; A61K 9/00; A61K 9/0021; A61K 9/70; A61K 9/7007; A61M 37/00;
(Continued)

(56) References Cited

U.S. PATENT DOCUMENTS 11,642,506 B1 *  5/2023  Liu ................. A61K 47/26
                                                      604/173
2001/0001669 A1 *  5/2001  DeVore ............ A61K 9/7007
                                                      530/356
(Continued)

FOREIGN PATENT DOCUMENTS

CA       2650197 A1 *  2/2008  ............ A61K 38/29
CN       105126243 A    12/2015
(Continued)

OTHER PUBLICATIONS

International Search Report for PCT/KR2017/004084 mailed Sep. 21, 2017 from Korean Intellectual Property Office.
(Continued)

*Primary Examiner* — Nathan R Price
*Assistant Examiner* — Mark A Ibel
(74) *Attorney, Agent, or Firm* — Revolution IP, PLLC

(57) ABSTRACT

A nucleic acid film fabrication method, includes: a mixing step in which a nucleic acid is added in powder form to distilled water or deionized water to prepare a mixed solution; a stirring step in which the mixed solution is stirred; a mixed solution application step in which the mixed solution is applied to a mold corresponding in shape to a final product of a nucleic acid film; and a drying step in which the mixed
(Continued)

solution applied to the mold is dried to be formed into the nucleic acid film, wherein the mold has a groove formed thereon in a thickness direction thereof, such that the nucleic acid film passing through the drying step has a protrusion protruding from one surface thereof toward human skin to correspond to the groove.

11 Claims, 12 Drawing Sheets

(51) Int. Cl.
  *A61K 9/70* (2006.01)
  *A61M 37/00* (2006.01)
  *B29C 39/02* (2006.01)
  *B29L 31/00* (2006.01)

(52) U.S. Cl.
  CPC ........... *A61K 9/7007* (2013.01); *A61M 37/00* (2013.01); *A61M 37/0015* (2013.01); *B29C 39/026* (2013.01); *A61M 2037/0023* (2013.01); *A61M 2037/0046* (2013.01); *B29K 2089/00* (2013.01); *B29L 2031/7544* (2013.01); *B29L 2031/756* (2013.01)

(58) Field of Classification Search
  CPC ...... A61M 37/0015; A61M 2037/0023; A61M 2037/0046; B29C 39/026; B29K 2089/00
  See application file for complete search history.

(56) References Cited

U.S. PATENT DOCUMENTS

| | | | |
|---|---|---|---|
| 2002/0132008 A1* | 9/2002 | Mumper | A61K 9/06 424/487 |
| 2004/0260251 A1* | 12/2004 | Chang | B81C 1/00111 604/272 |
| 2006/0047242 A1* | 3/2006 | Laurent | A61K 9/7023 604/46 |
| 2007/0172432 A1* | 7/2007 | Stopek | A61K 9/122 424/47 |
| 2008/0102192 A1 | 5/2008 | Johnson | |
| 2008/0269685 A1* | 10/2008 | Singh | A61K 38/29 604/173 |
| 2012/0027837 A1 | 2/2012 | DeMuth | |
| 2014/0276589 A1* | 9/2014 | Bayramov | A61K 9/0021 604/173 |
| 2017/0020942 A1 | 1/2017 | Naheed | |
| 2017/0050010 A1* | 2/2017 | Mcallister | A61M 37/0015 |
| 2017/0189660 A1 | 7/2017 | Baek | |
| 2017/0189661 A1 | 7/2017 | Lee | |
| 2023/0015942 A1* | 1/2023 | Lee | A61L 27/34 |
| 2023/0218507 A1* | 7/2023 | Gu | A61M 37/0015 |

FOREIGN PATENT DOCUMENTS

| | | | | |
|---|---|---|---|---|
| JP | 2000-325082 A | 11/2000 | | |
| JP | 2001-081098 A | 3/2001 | | |
| JP | 2002-124126 A | 4/2002 | | |
| JP | 2003-063924 A | 3/2003 | | |
| JP | 2004-531578 A | 10/2004 | | |
| JP | 2005-278444 A | 10/2005 | | |
| JP | 4629825 B2 | 2/2011 | | |
| JP | 2011-156370 A | 8/2011 | | |
| JP | 2011-172968 A | 9/2011 | | |
| JP | 2013-532997 A | 8/2013 | | |
| JP | 2015-217043 A | 12/2015 | | |
| KR | 10-2015-0138647 A | 12/2015 | | |
| KR | 10-1713119 B1 | 3/2017 | | |
| WO | WO-2004019885 A2 * | 3/2004 | ............. | A23L 27/79 |
| WO | WO-2007140483 A2 * | 12/2007 | ........... | A61K 31/337 |
| WO | 2008/130587 A2 | 10/2008 | | |
| WO | 2009/142741 A1 | 11/2009 | | |

OTHER PUBLICATIONS

Koen van der Maaden et al., "Microneedle technologies for (trans)dermal drug and vaccine delivery", Journal of Controlled Release, vol. 161, Issue 2, Jul. 20, 2012, pp. 645-655.

* cited by examiner

FIG. 3
(a)
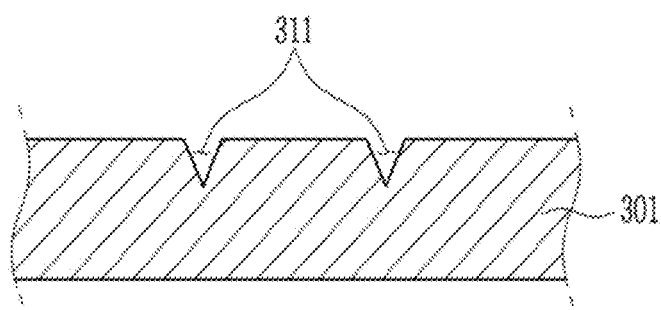
(b)
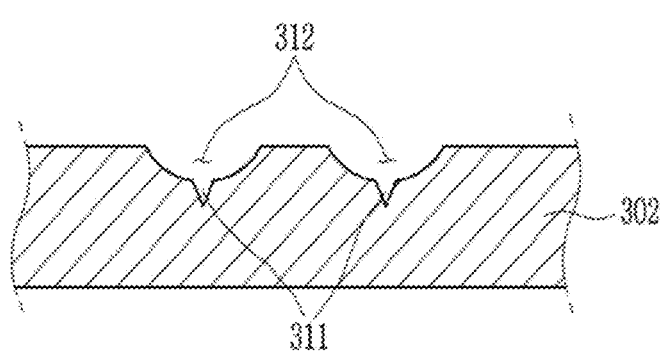
(c)
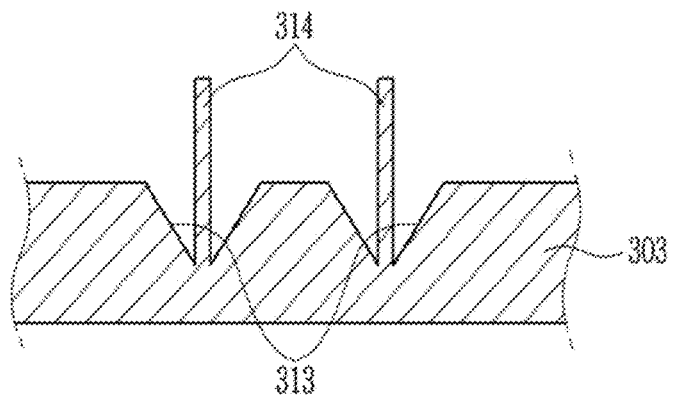

FIG. 13
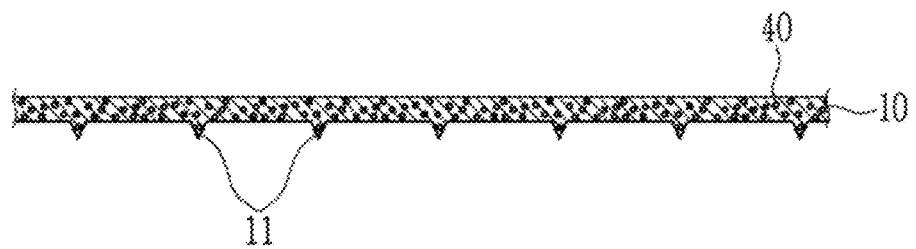
(a)
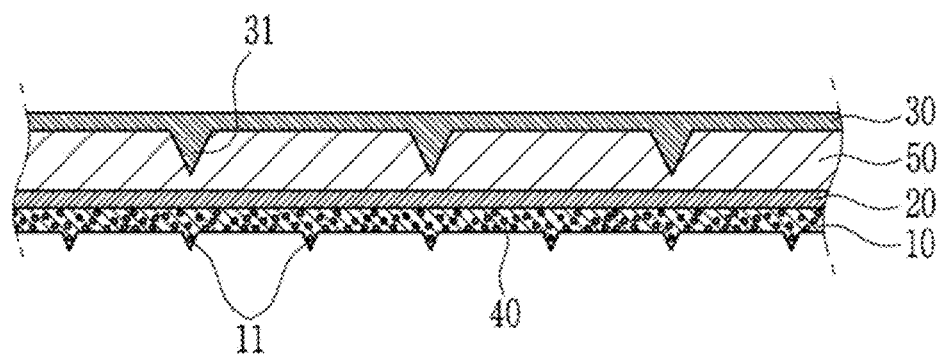

METHOD FOR MANUFACTURING NUCLEIC ACID FILM AND APPARATUS FOR INJECTING MEDICINE USING NUCLEIC ACID FILM

CROSS REFERENCE TO PRIOR APPLICATION

This application is a Division of U.S. patent application Ser. No. 16/091,521 filed on Oct. 5, 2018, which is a National Stage Patent Application of PCT International Patent Application No. PCT/KR2017/004084 filed on Apr. 14, 2017, which claims priority to Korean Patent Application Nos. 10-2016-0117332 filed on Sep. 12, 2016 and 10-2016-0046275 filed on Apr. 15, 2016 which are all hereby incorporated by reference in their entirety.

BACKGROUND

The present invention relates to a nucleic acid film fabrication method and a nucleic acid film-based drug administration device, and, more particularly, to a nucleic acid film fabrication method and nucleic acid film-based drug administration device which can be applied to a transdermal delivery technology relying on drug diffusion across the human skin so as to improve drug penetration into the skin while preventing skin problems.

Generally, most drugs are administered orally. However, when orally administered, some drugs, particularly protein and peptide drugs, cannot be effectively adsorbed due to severe decomposition in the gastrointestinal tract, poor absorption by the intestinal membranes, and/or interruption of first pass metabolism in the liver.

Another drug delivery technique is parenteral administration using a standard syringe or catheter. However, syringe injection causes needle phobia, substantial pain, and local damage to the skin in many patients. Collection of body fluids such as blood for diagnostic purposes causes similar anxieties. In addition, syringe injection is not ideal for continuous drug delivery or for continuous diagnosis.

Yet another drug delivery technique is transdermal delivery that commonly relies on drug diffusion across the skin. However, this method is not widely used due to insufficient permeability of the skin to many drugs. The outermost layer of the skin, that is, the horny layer is a primary barrier to transdermal drug penetration. Once a drug reaches the dermis (under the epithelium), the drug rapidly spreads into deep tissue layers and other parts of the body through blood circulation.

In an attempt to improve protein drug delivery through the skin, chemical enhancers, iontophoresis, electroporation, ultrasonication, and thermal elements have been used to supplement drug delivery. However, these techniques are not appropriate for certain drug forms and often do not provide therapeutic delivery. In addition, these techniques sometimes cause unwanted skin reactions and are impractical to control drug delivery over several hours or several days.

SUMMARY

Embodiments of the present invention provide a nucleic acid film fabrication method and nucleic acid film-based drug administration device which can be applied to a transdermal delivery technology relying on drug diffusion across the human skin so as to improve drug penetration into the skin while preventing skin problems.

In accordance with one aspect of the present invention, there is provided a nucleic acid film fabrication method including: a mixing step in which a nucleic acid is added in powder form to distilled water or deionized water to prepare a mixed solution; a stirring step in which the mixed solution is stirred; a mixed solution application step in which the mixed solution is applied to a mold corresponding in shape to a final product of a nucleic acid film; and a drying step in which the mixed solution applied to the mold is dried to be formed into the nucleic acid film.

The nucleic acid film passing through the drying step may have a microneedle or a drug delivery portion protruding from one surface thereof toward human skin and the nucleic acid film fabrication method may further include an oblique angle deposition step in which a coating layer is formed on the one surface of the nucleic acid film such that a tip of the microneedle or a tip of the drug delivery portion is exposed, after the drying step.

The mold may have a needle groove or a delivery groove formed thereon in a thickness direction thereof and the nucleic acid film fabrication method may further include an oblique angle deposition step in which a coating layer is formed on the mold excluding a bottom end of the needle groove or a bottom end of the delivery groove, before the mixed solution application step.

The nucleic acid film passing through the drying step may have a microneedle or a drug delivery portion protruding from one surface thereof toward human skin and the nucleic acid film fabrication method may further include an oblique angle deposition step in which a coating layer is formed on the one surface of the nucleic acid film such that a portion of the coating layer corresponding to the mirconeedle or a portion of the coating layer corresponding to the drug delivery portion is open, after the drying step.

The nucleic acid film fabrication method may further include: a finishing application step in which a finishing liquid is applied to cover the coating layer; and a finishing drying step in which the finishing liquid is dried to be formed into a finishing layer, after the oblique angle deposition step.

The nucleic acid film fabrication method may further include at least one of a film acquisition step in which the nucleic acid film is separated from the mold after the drying step; a mold preparation step in which the mold is machined to correspond in shape to the final product of the nucleic acid film before the mixed solution application step; and a surface treatment step in a surface of the mold is treated to be hydrophobic before the mixed solution application step.

In the mixing step, 1 part by weight to 100 parts by weight of a drug may be further added in liquid or capsule form to the mixed solution.

The nucleic acid may be extracted from at least one of by-products of marine food processing and by-products of plant food processing.

In accordance with another aspect of the present invention, there is provided a nucleic acid film-based drug administration device including: a nucleic acid film configured to contact the human skin and fabricated by the nucleic acid film fabrication method set forth above; a finishing film stacked on the nucleic acid film; and a drug filling a space between the nucleic acid film and the finishing film.

The nucleic acid film-based drug administration device may further include: a boundary film stacked between the nucleic acid film and the finishing film; and a decomposing liquid filling a space between the boundary film and the finishing film and comprising distilled water or deionized water, wherein the finishing film may include a perforation needle protruding therefrom toward the boundary film and configured to perforate the boundary film, and the drug may fill a space between the nucleic acid film and the boundary film.

In accordance with a further aspect of the present invention, there is provided a nucleic acid film-based drug administration device including a nucleic acid film fabricated by the nucleic acid film fabrication method in which, in the mixing step, 1 part by weight to 100 parts by weight of a drug is further added in liquid, powder, or capsule form to the mixed solution, and having a mirconeedle protruding from one surface thereof toward human skin.

The nucleic acid film-based drug administration device may further include: a boundary film stacked on the nucleic acid film; a finishing film stacked on the boundary film and including a perforation needle protruding therefrom toward the boundary film, the perforation needle being configured to perforate the boundary film; and a decomposing liquid filling a space between the boundary film and the finishing film and comprising distilled water or deionized water.

The nucleic acid film may include a buffer groove formed on the other surface thereof to correspond to the microneedle or the drug delivery portion.

The nucleic acid film-based drug administration device may further include a coating layer formed on the one surface of the nucleic acid film such that a tip of the microneedle is exposed or a tip of the drug delivery portion is exposed.

The nucleic acid film-based drug administration device may further include a coating layer formed on the one surface of the nucleic acid film such that a portion of the coating layer corresponding to the microneedle or a portion of the coating layer corresponding to the drug delivery portion is open.

The drug delivery portion may have a drug injection hole formed therethrough to allow the drug to be discharged through the drug injection hole.

The nucleic acid film may comprise a buffer groove formed on the other surface thereof to correspond to the microneedle or the drug delivery portion.

The nucleic acid film-based drug administration device may further include a coating layer formed on the other surface of the nucleic acid film such that a portion of the coating layer corresponding to the drug injection hole is open.

The nucleic acid film-based drug administration device may further include a protective film detachably coupled to the one surface of the nucleic acid film such that the drug injection hole is open or closed.

The nucleic acid film fabrication method and nucleic acid film-based drug administration device according to the present invention can be applied to transdermal delivery technology relying on drug diffusion across the human skin, thereby improving drug penetration into the skin while preventing skin problems.

In addition, a microneedle, a buffer groove, and a drug delivery portion having a drug injection hole 14 formed therethrough can be easily formed on a nucleic acid film and the nucleic acid film can have a uniform thickness.

Further, according to the present invention, the nucleic acid film can retain the shape thereof for a long time.

Moreover, according to the present invention, it is possible to prevent intrusion of foreign matter into the nucleic acid film while improving decomposition of the nucleic acid film.

Furthermore, a decomposing liquid can be stably supplied to the nucleic acid film, thereby enabling stable drug delivery.

In addition, depending on the form of drug delivery, the nucleic acid film can be patterned in various ways and the dosage of a drug can be adjusted according to the pattern of the nucleic acid film.

Further, according to the present invention, leakage of a drug through the drug injection hole and intrusion of foreign matter into the drug can be prevented while protecting the nucleic acid film.

BRIEF DESCRIPTION OF THE DRAWINGS

FIG. 3 is a sectional view of a mold used in the nucleic acid film fabrication method according to the first embodiment.

FIG. 13 is a sectional view of a nucleic acid film-based drug administration device according to a fourth embodiment of the present invention.

DETAILED DESCRIPTION

Figure 1:
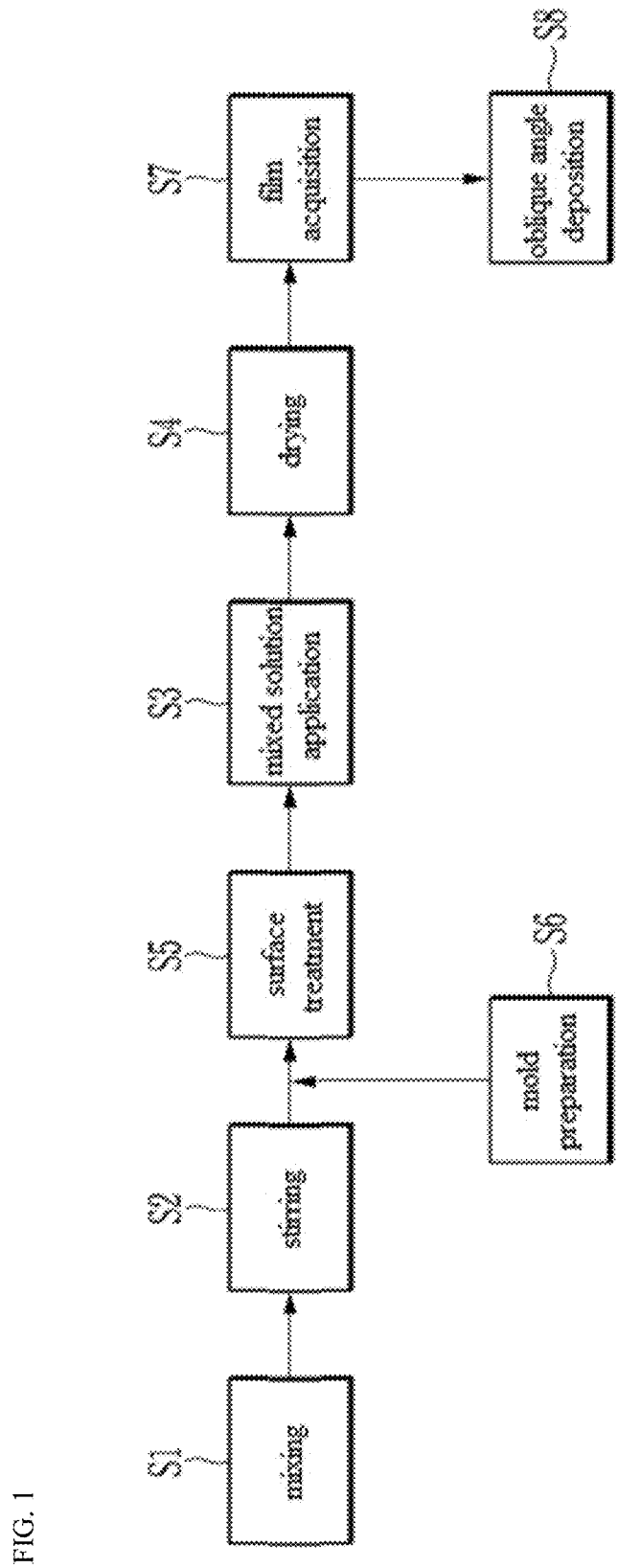
FIG. 1 is a flowchart of a nucleic acid film fabrication method according to a first embodiment of the present invention.

Hereinafter, embodiments of the present invention will be described with reference to the accompanying drawings. It should be understood that the present invention is not limited to the following embodiments and may be embodied in different ways.

In the drawings, portions irrelevant to the description will be omitted for clarity. Like components will be denoted by like reference numerals throughout the specification.

It will be understood that when an element is referred to as being "connected to" another element, it can be directly connected to the other element, or intervening elements may also be present. In addition, it will be understood that the terms "includes", "comprises", "including" and/or "comprising," when used in this specification, specify the presence of stated features, steps, operations, elements, and/or components, but do not preclude the presence or addition of one or more other features, steps, operations, elements, components, and/or groups.

It will be understood that when an element such as a layer, film, region or substrate is referred to as being placed "above"/"below" or "on"/"under" another element, it can be directly placed on the other element, or intervening layer(s) may also be present. In addition, spatially relative terms, such as "above," "upper (portion)," "upper surface," and the like may be understood as meaning "below," "lower (portion)," "lower surface," and the like according to a reference orientation. In other words, the expressions of spatial orientations are to be construed as indicating relative orientations instead of absolute orientations (that is, orientations with respect to the direction of gravity).

Figure 2:
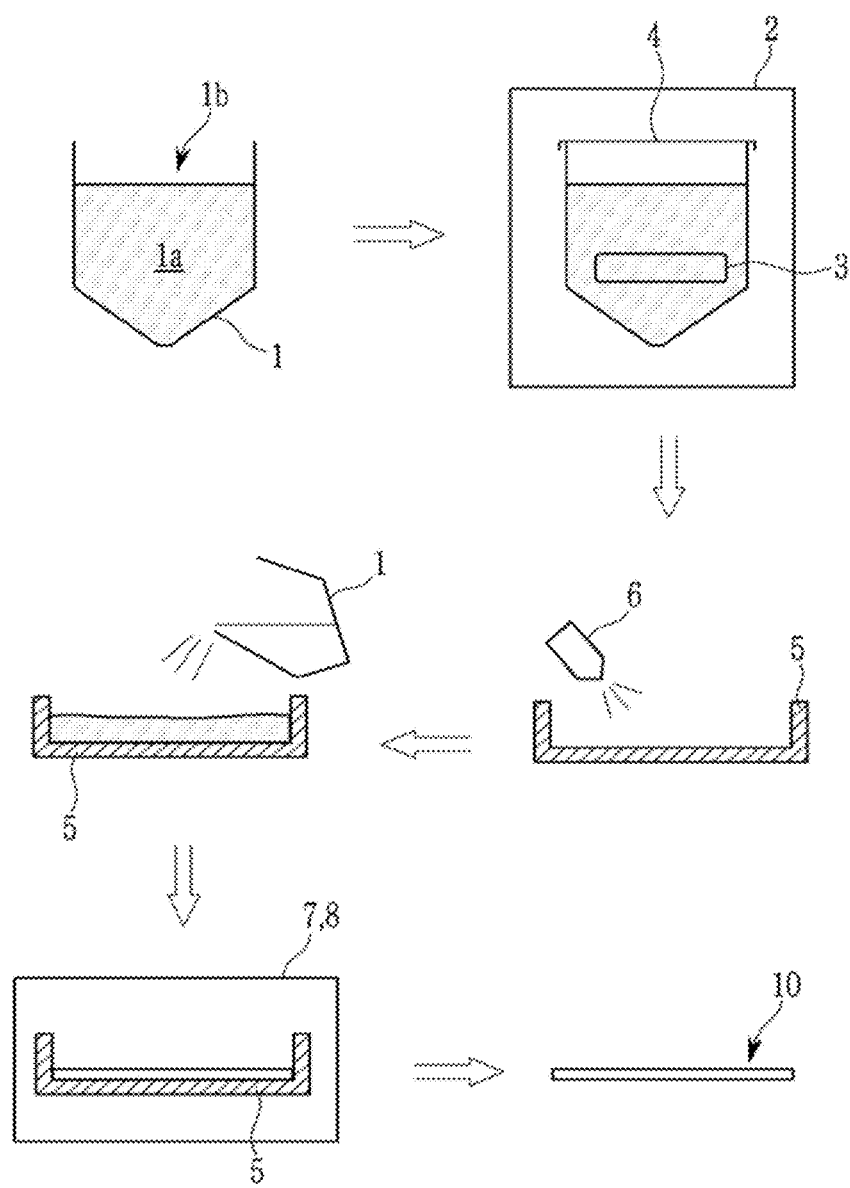
FIG. 2 is a view illustrating each process step of the nucleic acid film fabrication method according to the first embodiment.
Figure 4:
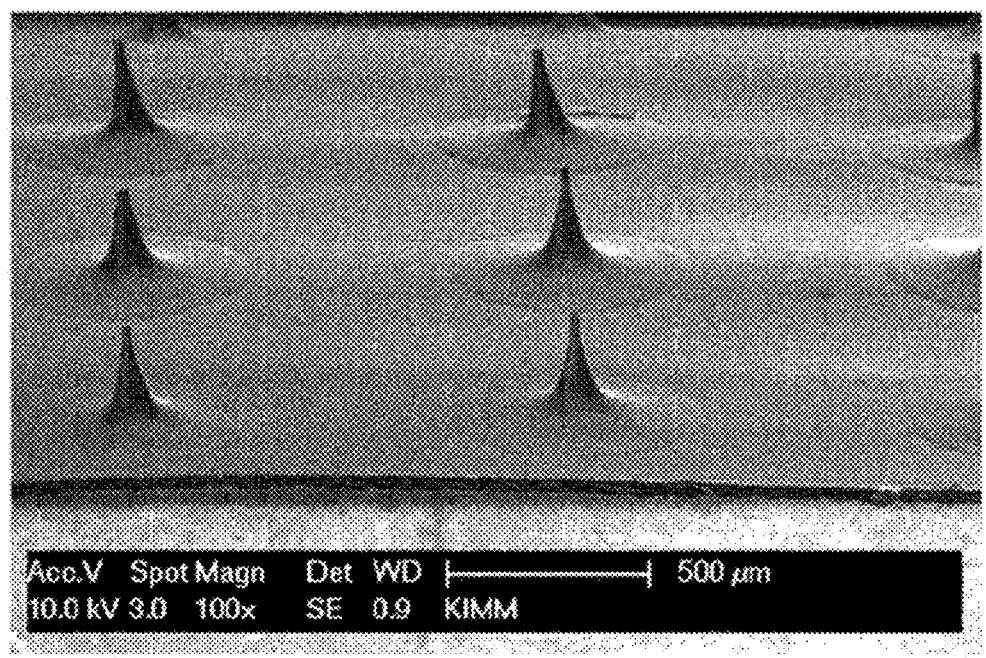
FIG. 4 is an image of a microneedle of a nucleic acid film fabricated by the nucleic acid film fabrication method according to the first embodiment.

Now, a nucleic acid film fabrication method according to a first embodiment of the present invention will be described. FIG. 1 is a flowchart of a nucleic acid film fabrication method according to a first embodiment of the present invention, FIG. 2 is a view illustrating each process in the nucleic acid film fabrication method according to the first embodiment, FIG. 3 is a sectional view of a mold used in the nucleic acid film fabrication method according to the first embodiment, FIG. 4 is an image of a microneedle of a nucleic acid film fabricated by the nucleic acid film fabrication method according to the first embodiment, and FIG. 5 is a view showing a process of directly forming a coating layer on a nucleic acid film in the nucleic acid film fabrication method according to the first embodiment.

Here, FIG. 3(a) is a view of a first mold 301 formed with a needle groove 311, FIG. 3(b) is a view of a second mold 302 formed with a buffer formation groove 312 and a needle groove 311, and FIG. 3(c) is a view of a third mold 303 formed with a delivery groove 313 and an injection protrusion 314, wherein the first to third molds are used as a mold 5 according to the present invention.

Figure 5:
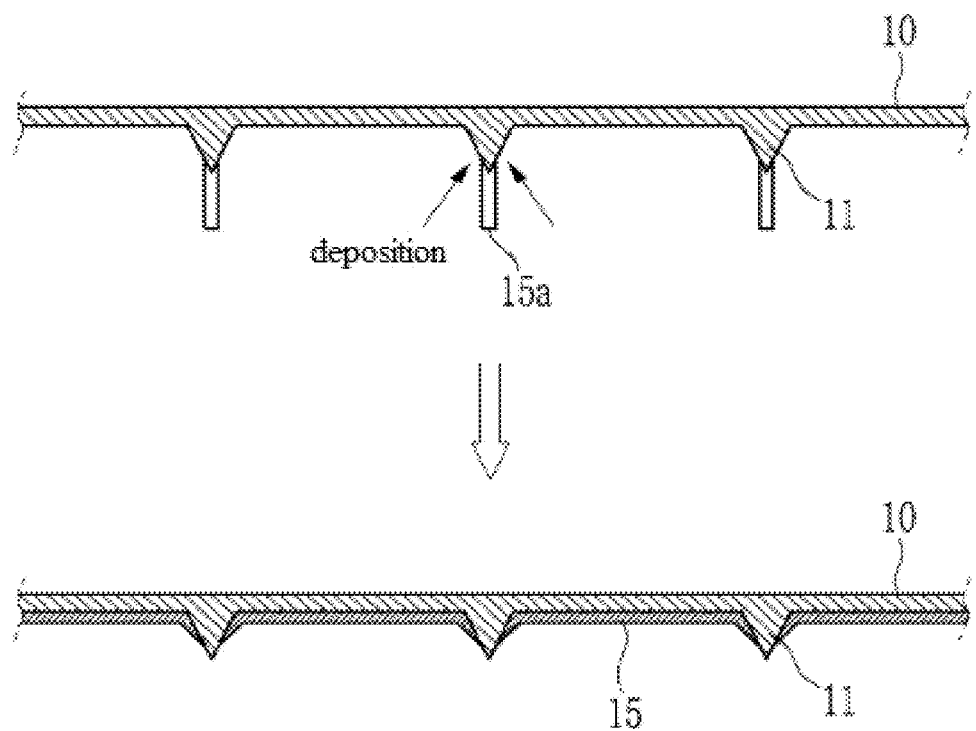
FIG. 5 is a view showing a process of directly forming a coating layer on a nucleic acid film in the nucleic acid film fabrication method according to the first embodiment.

In addition, the top of FIG. 5 shows an oblique angle deposition process for forming a coating layer 15 on a final product of a nucleic acid film 10 and the bottom of FIG. 5 shows a state in which the coating layer 15 is secured to the final product of the nucleic acid film 10.

Referring to FIG. 1 to FIG. 5, in the nucleic acid film fabrication method according to the first embodiment of the invention, the nucleic acid film 10 is fabricated using a powdery nucleic acid 1b.

Here, the nucleic acid 1b may be extracted from at least one of by-products of marine food processing and by-products of plant food processing.

Examples of the by-products of marine food processing may include salmon testes, salmon skins, pollack testes, crab carapaces, squid inks, and mixtures thereof.

Examples of the by-products of plant food processing may include yeasts of cereal crops or seed grains, such as brewer's yeast, rice yeast, and barley yeast, and mixtures thereof.

Specifically, the nucleic acid 1b may include a salmon nucleic acid extracted from salmon, among the by-products of marine food processing. When the nucleic acid 1b includes a salmon nucleic acid, poly deoxy ribo nucleotide (PDRN) in the salmon nucleic acid can help treatment of wounds and scars and skin regeneration without addition of specific drugs. In addition, the salmon nucleic acid can help to quickly heal skin wounds caused by a microneedle after removing a drug administration device from the human skin.

The nucleic acid film fabrication method according to the first embodiment includes a mixing step (S1), a stirring step (S2), a mixed solution application step (S3), and a drying step (S4).

In the mixing step (S1), a mixed solution is prepared by adding the nucleic acid 1b to an aqueous solution 1a in a mixing container 1.

The mixing container 1 is reduced in width toward the bottom thereof, such that the aqueous solution 1a and the nucleic acid 1b can be stably stirred. Here, the aqueous solution 1a may include distilled water or deionized water and the nucleic acid 1b may be provided in powder form.

Specifically, the mixed solution is prepared by adding 0.5 parts by weight to 5 parts by weight of the nucleic acid 1b to 100 parts by weight of the aqueous solution 1a (distilled water or deionized water). Here, the amount of the nucleic acid 1b may be adjusted according to the thickness of the final product of the nucleic acid film 10.

By way of one example, the nucleic acid 1b may be present in an amount of 0.5 parts by weight to 2 parts by weight relative to 100 parts by weight of the aqueous solution 1a. By way of another example, the nucleic acid 1b may be present in an amount of 1 part by weight to 3 parts by weight relative to 100 parts by weight of the aqueous solution 1a. By way of a further example, the nucleic acid 1b may be present in an amount of 0.5 parts by weight to 3 parts by weight relative to 100 parts by weight of the aqueous solution 1a. In other words, the amount of the nucleic acid 1b may be changed in multiples of 0.5 parts by weight within a range of 0.5 parts by weight to 5 parts by weight.

If the amount of the nucleic acid 1b is outside the predetermined range set forth above, the final product of the nucleic acid film 10 can have holes, cannot have a film shape, or can have cracks. In addition, when the final product of the nucleic acid film 10 is in use, it takes a long time for the final product of the nucleic acid film 10 to be decomposed, causing a delay in penetration of a drug into the skin.

Conversely, when the amount of the nucleic acid 1b falls within the predetermined range, the final product of the nucleic acid film 10 can stably have a film shape without any cracks and can be decomposed in a predetermined period of time using a decomposing liquid 50 described below, thereby improving penetration of a drug into the skin.

In order to prevent the aqueous solution 1a and the nucleic acid 1b from being contaminated during mixing of the aqueous solution 1a and the nucleic acid 1b, the mixing container 1 may be washed in advance with deionized water, isopropyl alcohol, acetone, and deionized water, in that order.

Particularly, in the mixing step (S1), 1 part by weight to 100 parts by weight of a drug 40 is further added in liquid, powder, or capsule form to the mixed solution. In other words, the amount of the drug 40 may be changed in multiples of 0.5 parts by weight within a range of 1 part by weight to 100 parts by weight relative to 100 parts by weight of the mixed solution. In addition, the amount of the drug 40 may be adjusted according to a desired dosage of the drug into the human skin.

In this way, since both the nucleic acid 1b and the drug 40 are mixed with the aqueous solution 1a, it is possible to obtain a final product of the nucleic acid film 10 in which the nucleic acid 1b is integrated with the drug 40.

In the stirring step (S2), the mixed solution obtained through the mixing step (S1) is stirred. In the stirring step (S2), the mixing container 1 is sealed with a sealant 4 such as Parafilm, followed by stirring the mixed solution in a stirring unit 2.

For example, the stirring unit 2 may be a magnetic stirrer, wherein a magnet 3 of the magnetic stirrer may be immersed in the mixed solution in the mixing container 1 after being washed with deionized water. It should be understood that the mixing container may be sealed with the sealant 4 after immersing the magnet 3 in the mixed solution.

In the stirring step (S2), the mixed solution is rotated only in one direction to retain a conical shape, such that the nucleic acid 1b is uniformly mixed in the mixed solution.

In the stirring step (S2), stirring of the mixed solution is performed at 600 rpm to 1000 rpm for 10 to 24 hours. For example, in the stirring step (S2), the mixed solution may be stirred at 700 rpm for 1 to 1.5 hours, followed by further stirring at 900 rpm for 9 to 10 hours.

In addition, in the stirring step (S2), the mixed solution may be allowed to stand for a predetermined period of time in a space shielded from UV light and sunlight so as to stabilize the mixed phase of the mixed solution.

In the mixed solution application step (S3), the mixed solution passing through the stirring step (S2) is applied to the mold 5. Here, the mold 5 may have a shape corresponding to the shape of the final product of the nucleic acid film 10.

The amount of the mixed solution applied to the mold 5 may be adjusted according to the size and thickness of the final product of the nucleic acid film 10.

In the mixed solution application step (S3), after applying the mixed solution to the mold 5, vacuum treatment may be performed for about 1 hour (for example, 55 to 70 minutes) so as to keep the mixed solution applied to the mold 5 in a stable manner and to promote drying of the mixed solution.

In the drying step (S4), the mixed solution applied to the mold 5 is dried to be formed into the nucleic acid film 10. In the drying step (S4), the mold 5 having the mixed solution applied thereto is dried in a drying unit 7 at a predetermined temperature for a predetermined period of time.

The drying step (S4) may include drying the mold 5 having the mixed solution applied thereto in the drying unit 7 at a temperature of 40° C. to 60° C. for 2 to 4 days. For example, the drying step (S4) may include drying the mold 5 having the mixed solution applied thereto in the drying unit 7 at a temperature of 45° C. to 50° C. for 3 to 4 days. If the temperature of the drying unit 7 is below the lower limit of the temperature range set forth above, the time required for drying can be increased, whereas, if the temperature of the drying unit 7 exceeds the upper limit of the temperature range set forth above, the final product of the nucleic acid film 10 can have defects such as cracks.

When the drying step (S4) is performed at the predetermined temperature for the predetermined period of time as set forth above, the final product of the nucleic acid film 10 can have a stable structure.

In the drying step (S4), bubbles may be removed from the mixed solution dried in the mold 5 using a pipetting unit 8.

The nucleic acid film fabrication method according to the first embodiment may further include at least one of a surface treatment step (S5), a mold preparation step (S6), a film acquisition step (S7), and an oblique angle deposition step (S8).

In the surface treatment step (S5), a surface of the mold 5 is treated to be hydrophobic prior to the mixed solution application step (S3). In the surface treatment step (S5), the surface of the mold 5 may be treated to be hydrophobic using a surface treatment unit 6 generating oxygen plasma. In the surface treatment step (S5), the mold 5 subjected to surface-treatment using the surface treatment unit 6 may be dried at room temperature for about 1 day.

Through the surface treatment step (S5), a hydrophilic surface of the mold 5 can be turned hydrophobic, while the mixed solution can be applied to the mold 5 to a uniform thickness.

In addition, due to hydrophobicity of the surface of the mold 5, a virtual membrane is formed between the mixed solution and the mold 5, thereby allowing the final product of the nucleic acid film 10 to be safely separated from the mold 5.

In the mold preparation step S6, the mold 5 is subjected to machining to correspond in shape to the final product of the nucleic acid film 10, before the mixed solution application step (S3), more specifically, before the surface treatment step (S5).

By way of one example, in the mold preparation step (S6), the mold 5 may be machined to have a flat surface.

By way of another example, in the mold preparation step (S6), the mold 5 may be machined to have a needle groove 311. Such a mold 5 will be referred to as a first mold 301. That is, the first mold 301 has a needle groove 311 formed on a surface thereof to be tapered in a thickness direction thereof, as shown in FIG. 3(a). Accordingly, the final product of the nucleic acid film 10 includes a microneedle 11 protruding therefrom.

By way of a further example, in the mold preparation step (S6), the mold 5 may be machined to have a buffer formation groove 312. Such a mold 5 will be referred to as a second mold 302. That is, the second mold 302 has a buffer formation groove 312 formed on a surface thereof, as shown in FIG. 3(b), wherein the buffer formation groove corresponds to a portion of the final product of the nucleic acid film configured to receive the drug 40. In addition, a needle groove 311 may be further formed on the buffer formation groove 312. Accordingly, the final product of the nucleic acid film 10 includes a buffer groove 12 formed convex toward the human skin and a microneedle 11 protruding from an outer surface of the buffer groove 12 toward the human skin.

By way of yet another example, in the mold preparation step (S6), the mold 5 may be machined to have a delivery groove 313 and an injection protrusion 314 formed on the delivery groove 313. Such a mold 5 will be referred to as a third mold 303. That is, the third mold 303 has a delivery groove 313 formed on the surface thereof to be tapered in a thickness direction thereof and the injection protrusion 314 protruding from the delivery groove 313. Accordingly, the final product of the nucleic acid film 10 includes a drug delivery portion 13 protruding from a surface thereof and a drug injection hole 15 passing through the drug delivery portion 13.

In the film acquisition step (S7), the nucleic acid film 10 passing through the drying step (S4) is separated from the mold 5. Through the film acquisition step S7, it is possible to obtain the nucleic acid film 10 having a predetermined thickness. Here, the nucleic acid film 10 may have a thickness of 10 nanometers to several hundred micrometers. For example, the nucleic acid film 10 may have a thickness of several hundred nanometers.

In the oblique angle deposition step (S8), a coating layer 15 is formed on the final product of the nucleic acid film 10. The coating layer 15 may be formed of an inorganic or organic material which is not decomposed by the decomposing liquid 50 described below and is harmless to humans. For example, the coating layer 15 may contain a material such as gold, silver, etc. as a main ingredient. Through the oblique angle deposition step (S8), the nucleic acid film 10 can retain a shape thereof in a stable manner. Particularly, through the oblique angle deposition step (S8), the geometries of the microneedle 11, the buffer groove 12, and the drug delivery portion 13 protruding from the nucleic acid film 10 can be maintained for a long time, while the nucleic acid film 10 can remain flat or remain held against the human body for a long time.

The oblique angle deposition step (S8) is performed for the final product of the nucleic acid film 10 obtained by applying the mixed solution to the mold 5, that is, the first mold 301, the second mold 302, or the third mold 303, followed by the drying step (S4) or the film acquisition step (S7), as shown in FIG. 1 and FIG. 5.

Here, the final product of the nucleic acid film 10 obtained through the drying step (S4) or the film acquisition step (S7) includes the microneedle 11 or the drug delivery portion 13 extending therefrom toward the human skin.

In the oblique angle deposition step (S8), the coating layer 15 may be formed to cover at least the microneedle 11 such that a tip of the microneedle 11 is exposed or may be formed to cover at least the drug delivery portion 13 such that a tip of the drug delivery portion 13 is exposed. Particularly, for the nucleic acid film 10 formed with the drug delivery portion 13, the coating layer 15 is formed not to close the drug injection hole 14 described below.

In the oblique angle deposition step (S8), with the tip of the microneedle 11 covered with a first deposition aid member 15a, the coating layer 15 may be formed to cover at least the microneedle 11. In addition, in the oblique angle deposition step S8, with the tip of the drug delivery portion 13 covered with the first deposition aid member 15a, the coating layer 15 may be formed to cover at least the drug delivery portion 13. After formation of the coating layer 15 in the oblique angle deposition step (S8), the first deposition aid member 15a is removed from the nucleic acid film 10.

Firstly, for a final product of the nucleic acid film 10 obtained using the first mold 301, the phrase "the tip of the microneedle 11 or the tip of the drug delivery portion 13 is exposed" may mean that the coating layer 15 is formed on the final product of the nucleic acid film 10 in the following manner: The coating layer 15 may cover only the microneedle 11 excluding the tip of the microneedle 11, may cover the microneedle 11 excluding the tip of the microneedle 11 and a portion of one surface of the nucleic acid film 10 on which the microneedle 11 is formed, or may cover the microneedle 11 excluding the tip of the microneedle 11 and the entirety of one surface of the nucleic acid film 10 on which the microneedle 11 is formed.

Secondly, for a final product of the nucleic acid film 10 obtained using the second mold 302, the phrase "the tip of the microneedle 11 or the tip of the drug delivery portion 13 is exposed" may mean that the coating layer 15 is formed on the final nucleic acid film 10 in the following manner: The coating layer 15 may cover only an outer surface of the buffer groove 12, may cover the outer surface of the buffer groove 12 and the microneedle 11 excluding the end of the microneedle 11, may cover at least the outer surface of the buffer groove 12 and a portion of one surface of the nucleic acid film 10 on which the buffer groove 12 is formed, or may cover at least the outer surface of the buffer groove 12 and the entirety of one surface of the nucleic acid film 10 on which the buffer groove 12 is formed.

Thirdly, for a final nucleic acid film 10 obtained using the third mold 303, the phrase "the tip of the microneedle 11 or the tip of the drug delivery portion 13 is exposed" may mean that the coating layer 15 is formed on the final nucleic acid film 10 in the following manner: The coating layer 15 may cover only the drug delivery portion 13 excluding the tip of the drug delivery portion 13, may cover the drug delivery portion 13 excluding the tip of the drug delivery portion 13 and a portion of one surface of the nucleic acid film 10 on which the drug delivery portion 13 is formed, or may cover the drug delivery portion 13 excluding the end of drug delivery portion 13 and the entirety of one surface of the nucleic acid film 10 on which the drug delivery portion 13 is formed.

In this way, in the nucleic acid film fabrication method according to the first embodiment, the coating layer can be formed on the microneedle 11, the buffer groove 12, and the drug delivery portion 13 formed with the drug injection hole 14 of the final product of the nucleic acid film 10.

In the oblique angle deposition step (S8), any typical method such as oblique angle deposition, partial plating, partial coating, or sputtering may be employed to exclude the tip of the microneedle 11 or the tip of the drug delivery portion 13 from being covered with the coating layer. In the nucleic acid film fabrication method according to the first embodiment, oblique angle deposition is employed to exclude the tip of the microneedle 11 or the tip of the drug delivery portion 13 from being covered with the coating layer. The oblique angle deposition step S8 includes a process of curing the coating layer 15.

In this way, the coating layer 15 can be formed on the final product of the nucleic acid film 10 such that the tip of the microneedle 11 or the tip of the drug delivery portion 13 is exposed.

Figure 6:
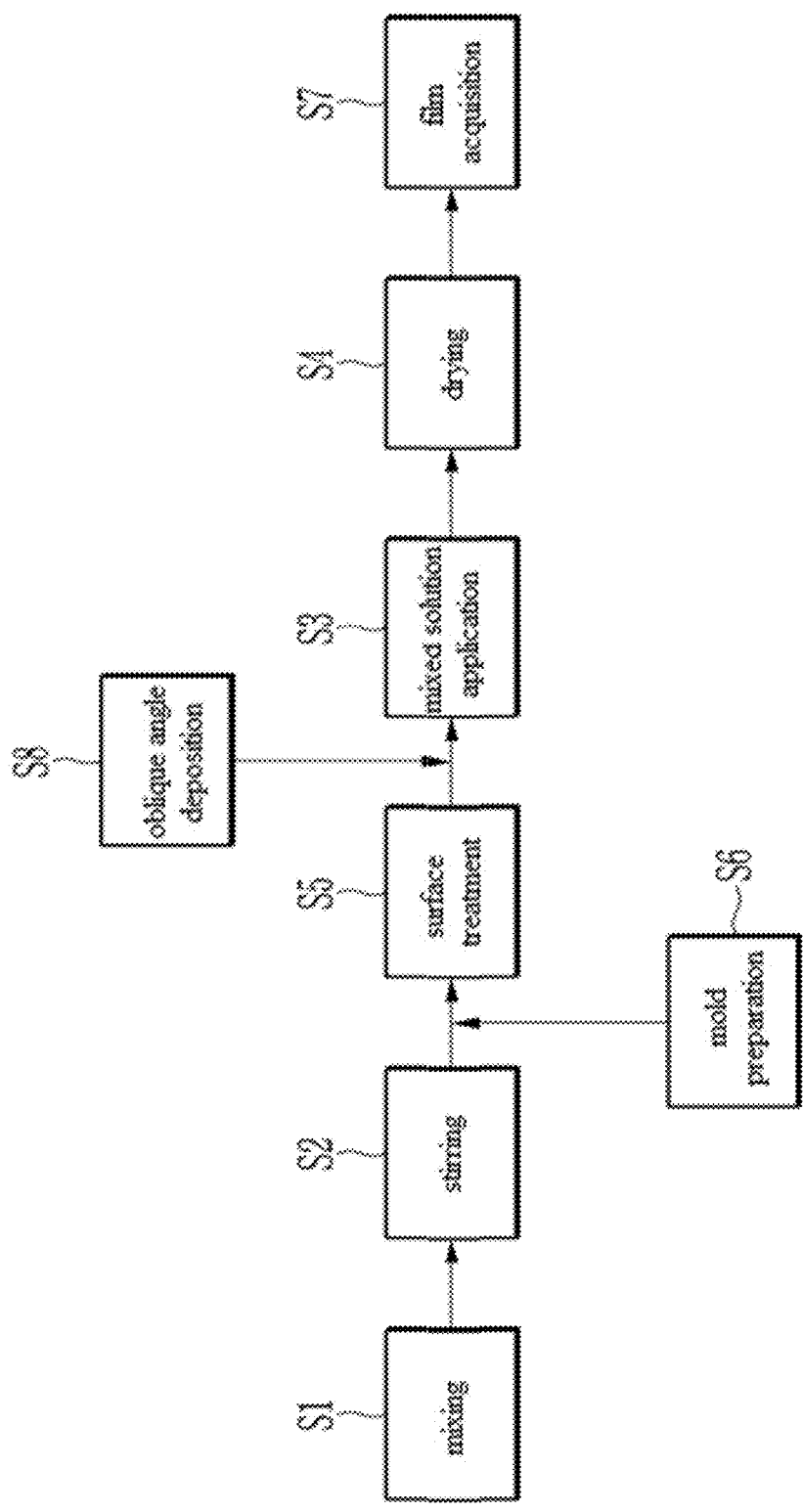
FIG. 6 is a flowchart of a nucleic acid film fabrication method according to a second embodiment.

Next, a nucleic acid film fabrication method according to a second embodiment of the present invention will be described. FIG. 6 is a flowchart of the nucleic acid film fabrication method according to the second embodiment and FIG. 7 shows a process of forming a coating layer on a nucleic acid film using a mold formed with the coating layer in the nucleic acid film fabrication method according to the second embodiment.

Figure 7:
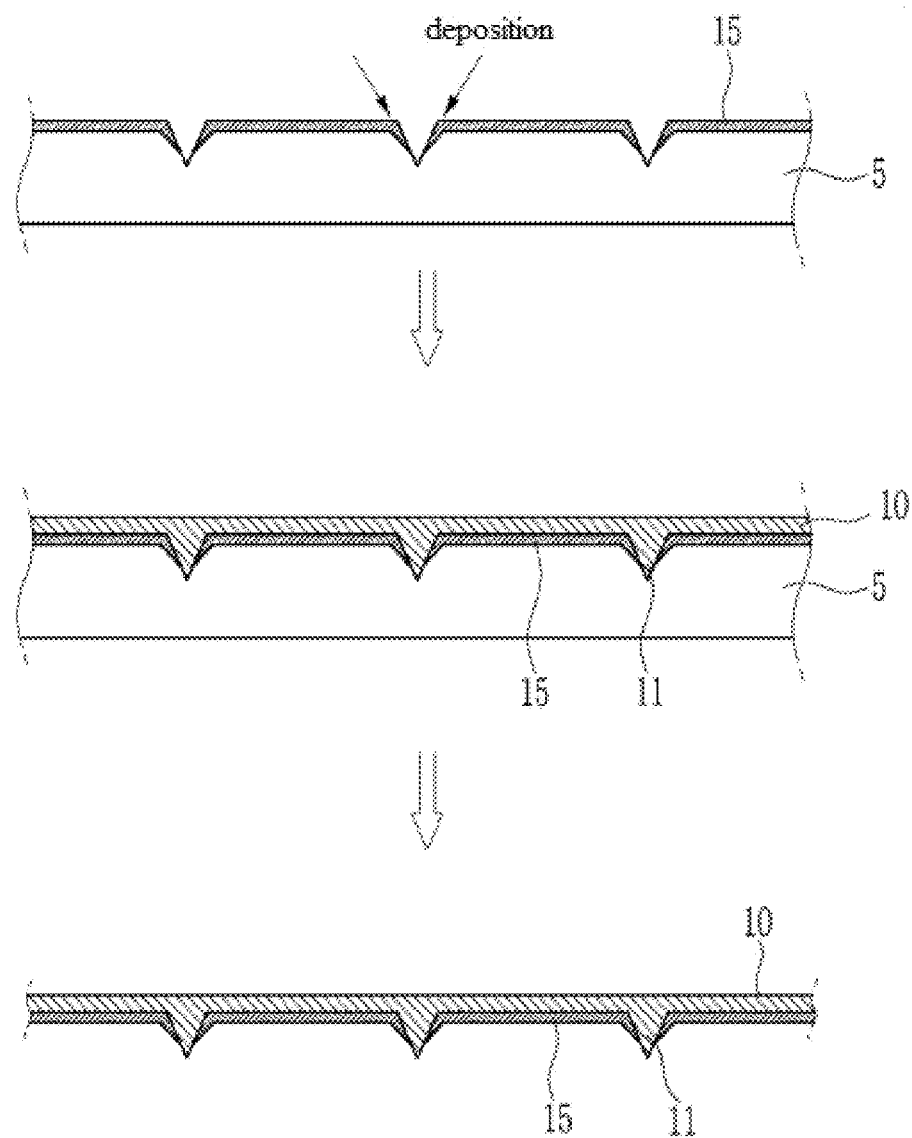
FIG. 7 shows a process of forming a coating layer on a nucleic acid film using a mold having the coating layer formed thereon in the nucleic acid film fabrication method according to the second embodiment.

Here, the top of FIG. 7 shows a coating layer 15 formed on a mold 5, the middle of FIG. 7 shows a nucleic acid film 10 stacked on the mold 5 formed with the coating layer 15, and the bottom of FIG. 7 shows the nucleic acid film 10 and the coating layer 15 removed from the mold 5, wherein the coating layer 15 is secured to the nucleic acid film 10.

Referring to FIG. 6 and FIG. 7, the nucleic acid film fabrication method according to the second embodiment includes a mixing step (S1), a stirring step (S2), a mixed solution application step (S3), and a drying step (S4).

In addition, the nucleic acid film fabrication method according to the second embodiment may further include at least one of a surface treatment step (S5), a mold preparation step (S6), a film acquisition step (S7), and an oblique angle deposition step (S8).

With regard to the nucleic acid film fabrication method according to the second embodiment, the same components as those used in the nucleic acid film fabrication method according to the first embodiment will be denoted by the same reference numerals as in the first embodiment and description thereof will be omitted.

In the oblique angle deposition (S8) according to this embodiment, the coating layer 15 is secured to the nucleic acid film 10 after being formed on the mold 5.

The oblique angle deposition step (S8) is performed on the first mold 301 or the second mold 302, which is used as the mold 5 according to the present invention, prior to the mixed solution application step (S3). In other words, the oblique angle deposition step (S8) is performed on the first mold 301, the second mold 302, or the third mold 303, as the mold 5, after the surface treatment step (S5) and before the mixed solution application step (S3).

For example, in the mold preparation step (S6), a needle groove 311 tapered in a thickness direction thereof may be formed on the mold 5.

In the oblique angle deposition (S8), the coating layer 15 is formed at at least an entrance of the needle groove 311 excluding a bottom end of the needle groove 311.

By way of one example, with regard to the first mold 301, the phrase "excluding a bottom end of the needle groove 311" may mean that the coating layer 15 is formed on the first mold in the following manner: The coating layer 15 may be formed only at the entrance of the needle groove 311, may be formed at the entrance of the needle groove 311 and on a portion of one surface of the mold 5 on which the needle groove 311 is formed, or may be formed at the entrance of the needle groove 311 and on the entirety of one surface of the mold 5 on which the needle groove 311 is formed.

By way of another example, with regard to the second mold 302, the phrase "excluding a bottom end of the needle groove 311" may mean that the coating layer 15 is formed on the second mold in the following manner: The coating layer 15 may also be formed on the buffer formation groove 312. The coating layer 15 may be formed only on the buffer formation groove 312, may be formed on the buffer formation groove 312 and at the entrance of the needle groove 311, may be formed at least on the buffer formation groove 312 and on a portion of one surface of the mold 5 on which the buffer formation groove 312 is formed, or may be formed at least on the buffer formation groove 312 and on the entirety of one surface of the mold 5 on which the buffer formation groove 312 is formed.

By way of a further example, with regard to the third mold 303, the phrase "excluding a bottom end of the needle groove 311" may mean that the coating layer 15 is formed in the following manner: The coating layer 15 may also be formed on the delivery groove 313. The coating layer 15 may be formed only on the delivery groove 313, may be formed at least on the delivery groove 313 and on a portion of one surface of the mold 5 on which the delivery groove 313 is formed, or may be formed at least on the delivery groove 313 and on the entirety of one surface of the mold 5 on which the delivery groove 313 is formed. Here, the injection protrusion 314 is not involved in formation of the coating layer 15.

Although not shown in the drawings, in the oblique angle deposition step S8, with the bottom end of the needle groove 311, the bottom end of the buffer formation groove 312, or the bottom end of the delivery groove 313 covered with a separate deposition aid member (not shown), the coating layer 15 may be formed at the entrance of the needle groove 311 or the delivery groove 313, followed by removal of the deposition aid member.

In the oblique angle deposition step (S8), any typical method such as oblique angle deposition, partial plating, partial coating, or sputtering may be employed to exclude the bottom end of the needle groove 311, the bottom end of the buffer formation groove 312, or the bottom end of the delivery groove 313 from being covered with the coating layer. In the nucleic acid film fabrication method according to the second embodiment, oblique angle deposition is employed to form the coating layer 15. The oblique angle deposition step (S8) includes a process of curing the coating layer 15.

In the mixed solution application step (S3), the mixed solution is applied to the mold 5 while filling the needle groove 311, and, in the drying step (S4), the coating layer 15 is integrated with a final product of the nucleic acid film 10. Accordingly, in the film acquisition step (S7), the nucleic acid film 10 and the coating layer 15 integrated with each other are removed from the mold 5 at the same time.

In this way, the final product of the nucleic acid film 10 has the coating layer 15 formed thereon such that a tip of a microneedle 11 formed using the needle groove 311 is exposed.

Figure 8:
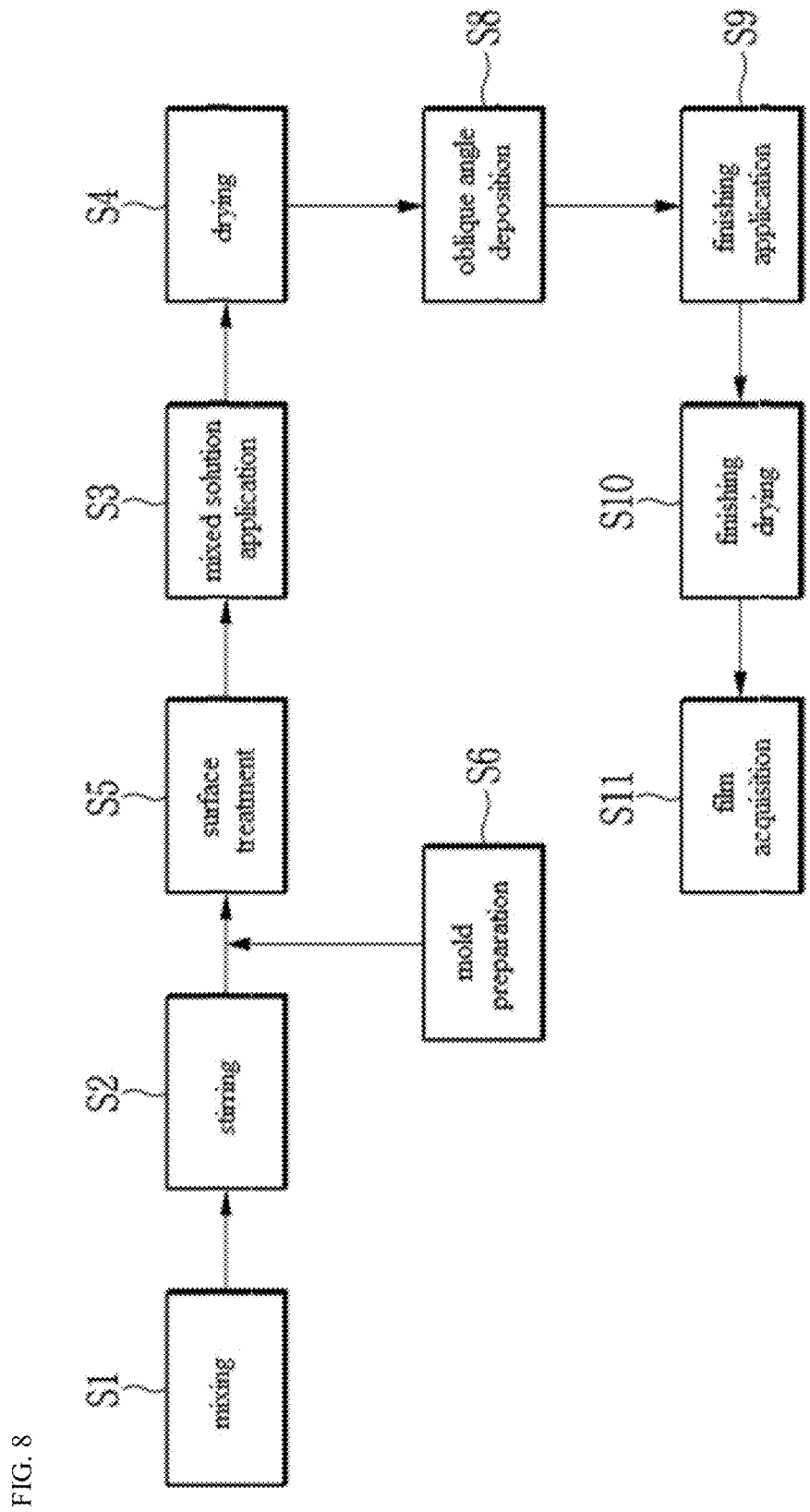
FIG. 8 is a flowchart of a nucleic acid film fabrication method according to a third embodiment of the present invention.

Next, a nucleic acid film fabrication method according to a third embodiment of the present invention will be described. FIG. 8 is a flowchart of a nucleic acid film fabrication method according to a third embodiment of the present invention and FIG. 9 is a view illustrating a process of embedding a coating layer in a nucleic acid film in the nucleic acid film fabrication method according to the third embodiment of the present invention.

Figure 9:
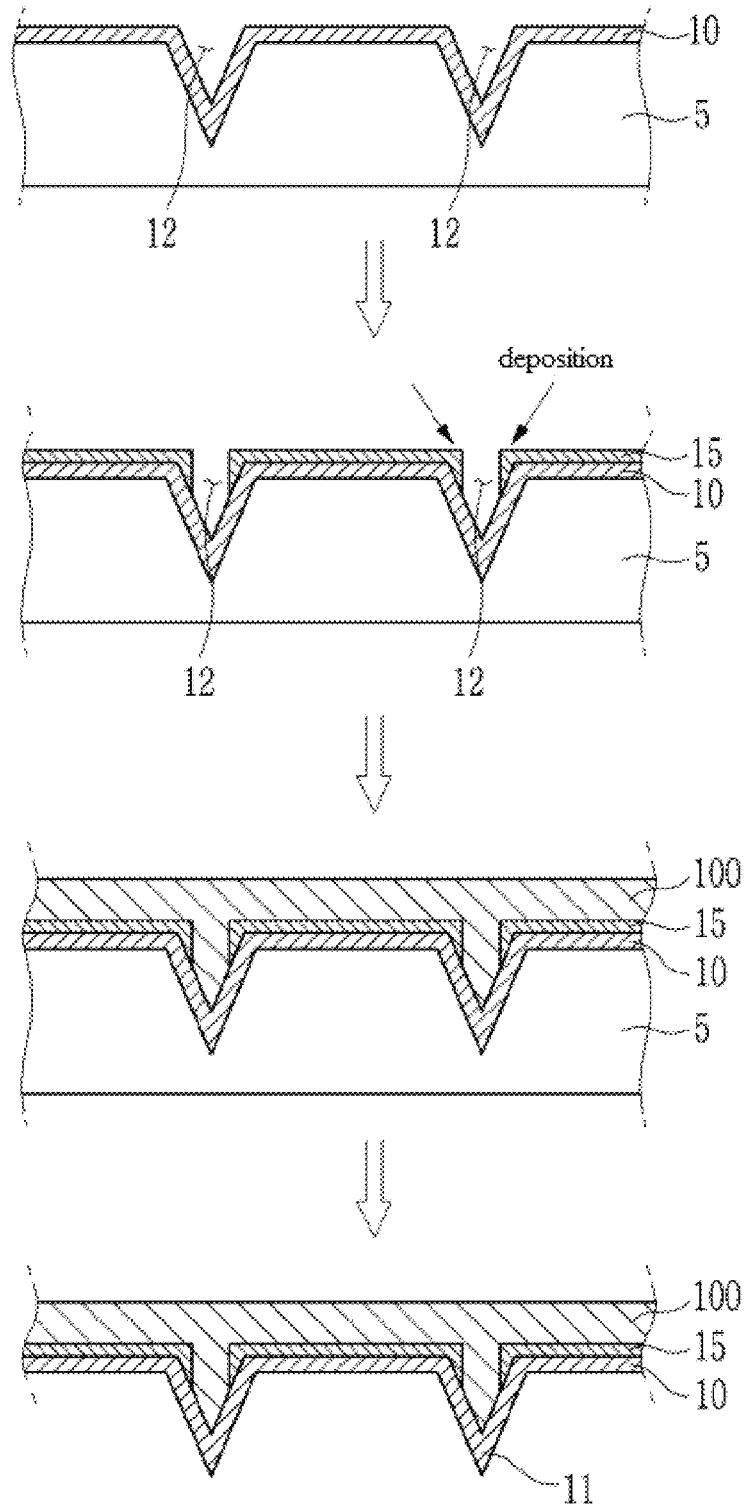
FIG. 9 is a view illustrating a process of embedding a coating layer in a nucleic acid film in the nucleic acid film fabrication method according to the third embodiment of the present invention.

Here, the top of FIG. 9 shows a nucleic acid film 10 having a buffer groove 12 formed thereon, the upper middle of FIG. 9 shows a coating layer 15 stacked on the nucleic acid film 10 having the buffer groove 12 formed thereon, the lower middle of FIG. 9 shows a finishing layer 100 stacked on the nucleic acid film 10 having the coating layer 15 stacked thereon, and the bottom of FIG. 9 shows the nucleic acid film 10 removed from a mold 5, wherein the coating layer 15 and the finishing layer 100 are secured to the nucleic acid film 10.

Referring to FIG. 8 and FIG. 9, the nucleic acid film fabrication method according to the third embodiment includes a mixing step (S1), a stirring step (S2), a mixed solution application step (S3), and a drying step (S4).

In addition, the nucleic acid film fabrication method according to the third embodiment may further include at least one of a surface treatment step (S5), a mold preparation step (S6), and a film acquisition step (S7).

With regard to the nucleic acid film fabrication method according to the third embodiment, the same components as those used in the nucleic acid film fabrication method according to the first or second embodiment will be denoted by the same reference numerals as in the first or second embodiment and description thereof will be omitted.

The nucleic acid film fabrication method according to the third embodiment may further include an oblique angle deposition step (S8), a finishing application step (S9) and a finishing drying step (S10).

In the nucleic acid film fabrication method according to the third embodiment, a coating layer 15 is stacked on a nucleic acid film 10, followed by stacking a finishing layer 100 thereon such that the coating layer 15 is embedded between the nucleic acid film 10 and the finishing layer 100.

By way of one example, a final product of the nucleic acid film 10 may include a microneedle 11 or a drug delivery portion 13 formed on one surface thereof. Thus, in the oblique angle deposition step (S8), the coating layer 15 is formed on the other surface of the nucleic acid film 10 such that a portion of the coating layer corresponding to the microneedle 11 or the drug delivery portion 13 is open. Then, in the finishing application step (S9), a finishing liquid is applied to the other surface of the nucleic acid film 10 on which the coating layer 15 is formed, and, in the finishing drying step (S10), the finishing liquid applied to the nucleic acid film 10 is dried to be formed into a finishing layer 100.

In this way, in the film acquisition step (S7), it is possible to obtain the nucleic acid film 10 including the coating layer 15 and the finishing layer 100 integrated therewith.

By way of another example, before the oblique angle deposition step (S8), the nucleic acid film 10 may include a microneedle 11 extending from one surface thereof toward the human skin and a buffer groove 12 formed on the other surface thereof to correspond to the microneedle 11 through the mixed solution application step (S3) and the drying step (S4).

Here, the buffer groove 12 may be formed using the second mold 302, which is used as the mold 5 according to the invention.

In addition, the buffer groove 12 may be formed through a process in which, after the mixed solution application step S3 or during the drying step (S4), a groove formation member (not shown) is inserted into the needle groove 311, the buffer formation groove 312, or the delivery groove 313, followed by removal of the groove formation member from the nucleic acid film 10 subsequent to the drying step (S4), as shown in the top of FIG. 9. Here, depending upon the intended use of the groove formation member 10a, the nucleic acid film 10 may be formed with the buffer groove 12 and the microneedle 11 or may be formed with the drug delivery portion 13 having the drug injection hole 14 formed therethrough.

After the drying step (S4), in the oblique angle deposition step (S8), the coating layer 15 is formed at at least an entrance of the buffer groove 12 excluding the bottom end of the buffer groove 12, as shown in FIG. 8 and FIG. 9.

Here, the phrase "excluding the bottom end of the buffer groove 12" means that the bottom end of the buffer groove 12 is open, and, more specifically, means that the coating layer 15 is formed on the nucleic acid film 10 in the following manner: The coating layer 15 may be formed only at the entrance of the buffer groove 12, may be formed at the entrance of the buffer groove 12 and on a portion of the other surface of the nucleic acid film 10 on which the buffer groove 12 is formed, or may be formed at the entrance of the buffer groove 12 and on the entirety of the other surface of the nucleic acid film 10 on which the buffer groove 12 is formed.

Although not shown in the drawings, the phase "excluding the bottom end of the buffer groove 12" may mean that the coating layer 15 is formed at least on an inner wall of the drug injection hole 14 such that the drug injection hole 14 can remain open.

Although not shown in the drawings, in the oblique angle deposition step (S8), with the bottom end of the buffer groove 12 covered with a separate deposition aid member (not shown), the coating layer 15 may be formed at the entrance of the buffer groove 12, followed by removal of the deposition aid member (not shown).

In the oblique angle deposition step (S8), any typical method such as oblique angle deposition, partial plating, partial coating, or sputtering may be employed may be employed to exclude the bottom end of the buffer groove 12 from being covered with the coating layer. In the nucleic acid film fabrication method according to the third embodiment, the coating layer 15 may be formed by oblique angle deposition. The oblique angle deposition step (S8) includes a process of curing the coating layer 15.

In the finishing application step (S9), a finishing liquid is applied to the mold 5 passing through the oblique angle deposition (S8) to fill the buffer groove 12 of the nucleic acid film 10 while covering the coating layer 15. Here, the finishing liquid is used to form the finishing layer 100 and may include the mixed solution set forth above for formation of a nucleic acid film or a mixed solution containing vitamins, collagen and the like for formation of a water-soluble functional film. In addition, the finishing liquid may contain a drug to be absorbed by the human body.

In the finishing drying step (S10), the finishing liquid applied to the mold 5 is dried to be transformed into the finishing layer 100. As a result, the finishing layer 100 may be formed into a nucleic acid film as set forth above or may be formed into a separate water-soluble functional film.

In this way, in the film acquisition step (S7), a final product of the nucleic acid film 10 having the coating layer 15 and the finishing layer 100 integrated therewith can be obtained. Here, the coating layer 15 is embedded between the finishing layer 100 and the nucleic acid film 10.

Although not shown in the drawings, the buffer groove 12 or the drug delivery portion 13 formed with the drug injection hole 14 may also be formed on the finishing layer 100 by utilizing the method of forming the buffer groove 12 on the nucleic acid film 10 as described in the third embodiment.

For example, the buffer groove 12 or the drug injection hole 14 may be formed on the finishing layer 100 through a process in which, after the finishing application step (S9) or during the finishing drying step (S10), a groove formation member (not shown) having a different size than the groove formation member inserted into the nucleic acid film 10 is inserted into the finishing layer 100, followed by removal of the groove formation member from the finishing layer 100 subsequent to the finishing drying step (S10).

Figure 10:
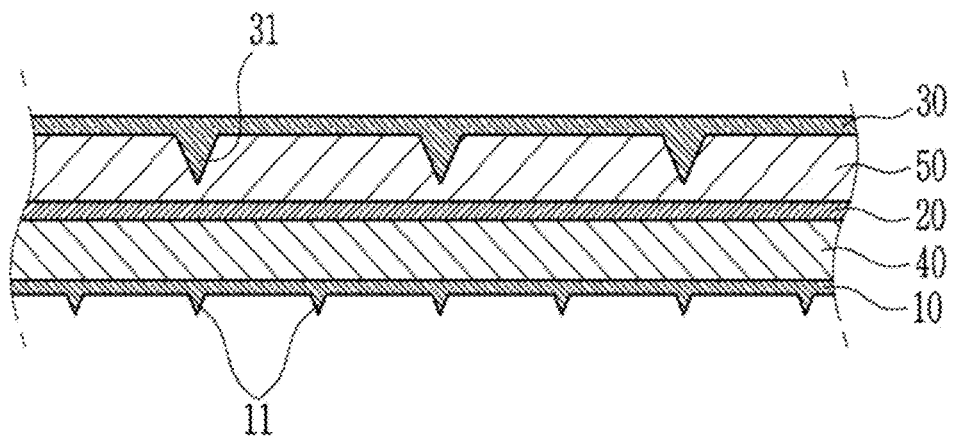
FIG. 10 is a sectional view of a nucleic acid film-based drug administration device according to a first embodiment of the present invention.

Next, a nucleic acid film-based drug administration device according to a first embodiment of the present invention will be described. FIG. 10 is a sectional view of a nucleic acid film-based drug administration device according to a first embodiment of the present invention. Referring to FIG. 1 to FIG. 10, the nucleic acid film-based drug administration device according to the first embodiment of the present invention includes a nucleic acid film 10 fabricated by any one of the nucleic acid film fabrication methods set forth above.

The nucleic acid film-based drug administration device according to the first embodiment includes the nucleic acid film 10, a finishing film 30, and a drug 40.

The nucleic acid film 10 is fabricated by any one of the nucleic acid film fabrication methods set forth above and is configured to contact the human skin. Here, the nucleic acid film 10 may include the microneedle 11 protruding therefrom, wherein the microneedle 11 is formed using the mold 5 formed with the needle groove 311. The microneedle 11 may extend from a surface of the nucleic acid film 10 toward the human skin.

Here, the microneedle 11 may be reduced in cross-sectional area with increasing distance from the surface of the nucleic acid film 10, that is, may have an inverted conical shape. A maximum diameter of the microneedle 11, that is, a diameter of the base of the microneedle adjoining the surface of the nucleic acid film 10 (the diameter of an imaginary circle in which the cross-sectional area of the microneedle 11 is inscribed), may range from 200 μm to 400 μm, a diameter of a tip of the microneedle 11 may range from 20 μm to 30 μm, and a height of the microneedle 11 from the surface of the nucleic acid film 10 may range from 200 μm to 300 μm. If the dimensions of the microneedle 11 are outside the aforementioned ranges, the microneedle 11 can collapse or can be bent with respect to the nucleic acid film 10. Conversely, when the dimensions of the microneedle 11 fall within the aforementioned ranges, the nucleic acid film 10 can retain a protruding shape thereof, can allow the drug 40 to easily penetrate the skin therethrough, can be prevented from being bent or broken when in use, and can be prevented from being broken when separated from the mold 5.

Although not shown in the drawings, the nucleic acid film 10 includes the coating layer 15 formed thereon such that the tip of the microneedle 11 is exposed. Here, the coating layer 15 may be formed on the nucleic acid film 10 by any one of the nucleic acid film fabrication methods set forth above.

In addition to the coating layer 15, the nucleic acid film 10 may further include the finishing layer 100 formed thereon. Here, the coating layer 15 and the finishing layer 100 may be formed on the nucleic acid film 10 by any one of the nucleic acid film fabrication methods set forth above.

With the coating layer 15, the strength of the microneedle 11 can be reinforced while the microneedle 11 can be prevented from being bent or broken.

The finishing film 30 is stacked and supported on the nucleic acid film 10. Here, the finishing film 30 may be configured in various ways without limitation, so long as the finishing film can prevent degeneration of the drug 40.

The drug 40 fills a space between the nucleic acid film 10 and the finishing film 30. Here, the drug 40 does not decompose the nucleic acid film 10. The drug 40 may be comprised of any one selected from therapeutic or health-aid drugs, including drugs for hormone regulation, anesthesia, anti-aging of skin, wrinkle removal, tattoo removal, tattoo formation, and sebum absorption. For example, the drug 40 may include hyaluronic acid for anti-aging or wrinkle removal.

When the nucleic acid film 10 is attached to the human skin, the drug 40 can penetrate the human skin as the nucleic acid film 10 is decomposed by moisture remaining on the surface of the nucleic acid film 10, moisture remaining on the human skin, or distilled water or deionized water applied to at least one of the nucleic acid film 10 and the human skin.

The nucleic acid film-based drug administration device according to the first embodiment may further include a boundary film 20. The boundary film 20 is stacked and supported between the nucleic acid film 10 and the finishing film 30. The drug 40 fills a space between the nucleic acid film 10 and the boundary film 20. In addition, a decomposing liquid 50 fills a space between the boundary film 20 and the finishing film 30. The decomposing liquid 50 may include distilled water or deionized water. Here, the finishing film 30 may include a perforation needle 31 protruding therefrom and configured to penetrate the boundary film 20.

When the drug administration device is attached to and pressed against the human skin, the decomposing liquid 50 is moved toward the drug 40 as the perforation needle 31 perforates the boundary film 20, such that the nucleic acid film 10 can be decomposed by the decomposing liquid 50 without separately applying distilled water or deionized water to the nucleic acid film 10, thereby allowing the drug 40 to penetrate the human skin.

Figure 11:
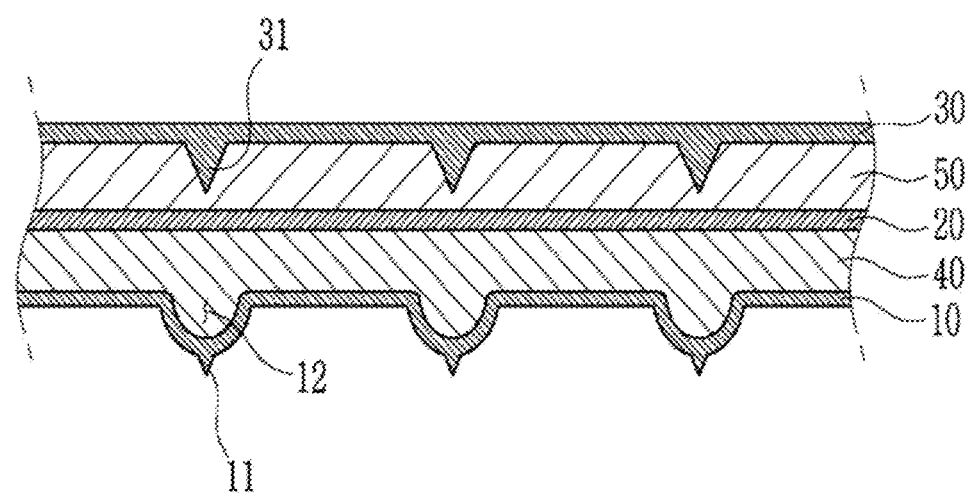
FIG. 11 is a sectional view of a nucleic acid film-based drug administration device according to a second embodiment of the present invention.

Next, a nucleic acid film-based drug administration device according to a second embodiment of the present invention will be described. FIG. 11 is a sectional view of a nucleic acid film-based drug administration device according to a second embodiment of the present invention. Referring to FIG. 1 to FIG. 9 and FIG. 11, the nucleic acid film-based drug administration device according to the second embodiment of the present invention includes a nucleic acid film 10 fabricated by any one of the nucleic acid film fabrication methods set forth above.

The nucleic acid film-based drug administration device according to the second embodiment includes the nucleic acid film 10, a boundary film 20, a finishing film 30, a drug 40, and a decomposing liquid 50.

The nucleic acid film 10 is fabricated by any one of the nucleic acid film fabrication methods set forth above and is configured to contact the human skin. The nucleic acid film 10 may have the buffer groove 12 formed thereon, wherein the buffer groove 12 is formed using the mold 5 formed with the buffer formation groove 312. The buffer groove 12 defines a space for receiving the drug 40. In addition, the nucleic acid film 10 may have the microneedle 11 protruding from the buffer groove 12, wherein the microneedle 11 is formed using the mold formed with the needle groove 311. Here, the buffer groove 12 is convex toward the human skin and the microneedle 11 extends from the buffer groove 12 toward the human skin.

The boundary film 20 is stacked and supported on the nucleic acid film 10. Here, the boundary film 20 may be configured in various ways without limitation, so long as the boundary film 20 can isolate the drug 40 from the decomposing liquid 50 and can be perforated by a perforation needle 31 protruding from the finishing film 30.

Although not shown in the drawings, the nucleic acid film 10 includes the coating layer 15 formed thereon in such a way that the tip of the microneedle 11 is exposed. Here, the coating layer 15 may be formed on the nucleic acid film 10 by any one of the nucleic acid film fabrication methods set forth above.

In addition to the coating layer 15, the nucleic acid film 10 may further include the finishing layer 100 formed thereon. Here, the coating layer 15 and the finishing layer 100 may be formed on the nucleic acid film 10 by any one of the nucleic acid film fabrication methods set forth above.

With the coating layer 15, the strength of the microneedle 11 can be reinforced while the microneedle 11 can be prevented from being bent or broken.

The finishing film 30 is stacked and supported on the boundary film 10. Here, the finishing film 30 may be configured in various ways without limitation, so long as the finishing film can prevent degeneration of the drug 40. The finishing film 30 may include a perforation needle 31 protruding therefrom and configured to perforate the boundary film 20.

The drug 40 fills a space between the nucleic acid film 10 and the boundary film 30. Here, the drug 40 does not decompose the nucleic acid film 10. The drug 40 may be comprised of any one selected from therapeutic or health-aid drugs, including drugs for hormone regulation, anesthesia, anti-aging of skin, wrinkle removal, tattoo removal, tattoo formation, and sebum absorption. For example, the drug 40 may include hyaluronic acid for anti-aging or wrinkle removal.

The decomposing liquid 50 fills a space between the boundary film 20 and the finishing film 30. The decomposing liquid 50 may include distilled water or deionized water.

When the drug administration device is attached to and pressed against the human skin, the decomposing liquid 50 is moved toward the drug 40 as the perforation needle 31 perforates the boundary film 20, such that the nucleic acid film 10 can be decomposed by the decomposing liquid 50 without separately applying distilled water or deionized water to the nucleic acid film 10, thereby allowing the drug 40 to penetrate the human skin.

Figure 12:
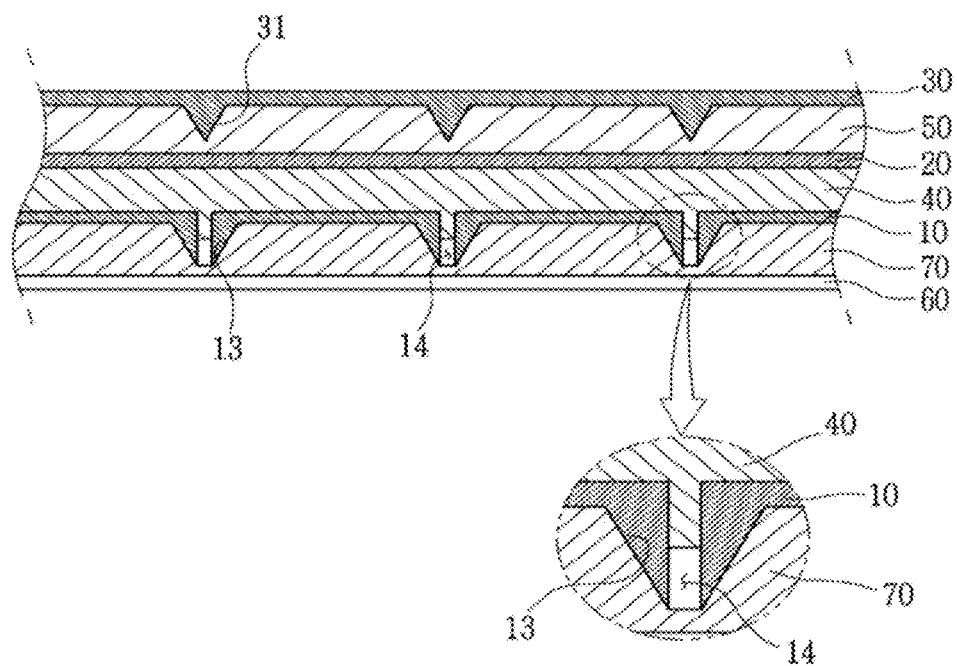
FIG. 12 is a sectional view of a nucleic acid film-based drug administration device according to a third embodiment of the present invention.

Next, a nucleic acid film-based drug administration device according to a third embodiment of the present invention will be described. FIG. 12 is a sectional view of a nucleic acid film-based drug administration device according to a third embodiment of the present invention. Referring to FIG. 1 to FIG. 9 and FIG. 12, the nucleic acid film-based drug administration device according to the third embodiment of the present invention includes a nucleic acid film 10 fabricated by any one of the nucleic acid film fabrication methods set forth above.

The nucleic acid film-based drug administration device according to the third embodiment includes the nucleic acid film 10, a boundary film 20, a finishing film 30, a drug 40, and a decomposing liquid 50.

The nucleic acid film 10 is fabricated by any one of the nucleic acid film fabrication methods set forth above and is configured to contact the human skin. The nucleic acid film 10 may have the drug delivery portion 13 protruding therefrom, wherein the drug delivery portion is formed using the mold 5 formed with the delivery groove 313. In addition, the nucleic acid film may have the drug injection hole 14 passing through the drug delivery portion 13, wherein the drug injection hole 14 is formed using the mold formed with the injection protrusion 314. Here, the drug delivery portion 13 extends from the nucleic acid film 10 toward the human skin and the drug injection hole 14 is configured such that leakage of the drug 40 therethrough can be prevented due to surface tension of the drug 40.

Although not shown in the drawings, the nucleic acid film 10 includes the coating layer 15 formed thereon such that the tip of the microneedle 11 is exposed. Here, the coating layer 15 may be formed on the nucleic acid film 10 by any one of the nucleic acid film fabrication methods set forth above.

In addition to the coating layer 15, the nucleic acid film 10 may further include the finishing layer 100 formed thereon. Here, the coating layer 15 and the finishing layer 100 may be formed on the nucleic acid film 10 by any one of the nucleic acid film fabrication methods set forth above.

With the coating layer 15, the strength of the microneedle 11 can be reinforced while the microneedle 11 can be prevented from being bent or broken.

The boundary film 20 is stacked and supported on the nucleic acid film 10. The boundary film 20 may be configured in various ways without limitation, so along as the boundary film can isolate the drug 40 from the decomposing liquid 50 and can be perforated by a perforation needle 31 protruding from the finishing film 30.

The finishing film 30 is stacked and supported on the boundary film 20. The finishing film 30 may be configured in various ways without limitation, so long as the finishing film can prevent degeneration of the drug 40. The finishing film 30 has the perforation needle 31 protruding therefrom and configured to perforate the boundary film 20.

The drug 40 fills a space between the nucleic acid film 10 and the boundary film 20. Here, the drug 40 does not decompose the nucleic acid film 10. The drug 40 may be comprised of any one selected from therapeutic or health-aid drugs, including drugs for hormone regulation, anesthesia, anti-aging of skin, wrinkle removal, tattoo removal, tattoo formation, and sebum absorption. For example, the drug 40 may include hyaluronic acid for anti-aging or wrinkle removal.

The decomposing liquid 50 fills a space between the boundary film 20 and the finishing film 30. The decomposing liquid 50 may include distilled water or deionized water.

When the drug administration device is attached to and pressed against the human skin, the decomposing liquid 50 is moved toward the drug 40 as the perforation needle 31 perforates the boundary film 20, such that the nucleic acid film 10 can be decomposed by the decomposing liquid 50 without separately applying distilled water or deionized water to the nucleic acid film 10, thereby allowing the drug 40 to penetrate the human skin.

The nucleic acid film-based drug administration device according to the third embodiment may further include a protective film 60 and a separation layer 70.

The protective film 60 is detachably coupled to the nucleic acid film 10 such that the drug injection hole 14 can be open or closed. In addition, the separation layer 70 is secured to the protective film 60 to be attached to or detached from the nucleic acid film 10. The separation layer 70 is configured not to be mixed with the drug 40.

The protective film 60 or the separation layer 70 further prevents leakage of the drug 40 through the drug injection hole 14 during transport or storage of the drug administration device while preventing intrusion of foreign matter into the drug injection hole 14.

Next, a nucleic acid film-based drug administration device according to a fourth embodiment of the present invention will be described. FIG. 13 is a sectional view of a nucleic acid film-based drug administration device according to a fourth embodiment of the present invention. Referring to FIG. 1 to FIG. 9 and FIG. 13, the nucleic acid film-based drug administration device according to the fourth embodiment includes a nucleic acid film 10 fabricated by the method in which the aqueous solution 1$a$ is mixed with the nucleic acid 1$b$ and the drug 40, among the nucleic acid film fabrication methods set forth above.

The nucleic acid film-based drug administration device according to the fourth embodiment includes the nucleic acid film 10. The nucleic acid film 10 may be fabricated by the method in which the aqueous solution 1$a$ is mixed with both the nucleic acid 1$b$ and the drug 40, among the nucleic acid film fabrication methods set forth above. Here, the nucleic acid film 10 may have the microneedle 11 protruding therefrom, wherein the microneedle 11 may be formed by the nucleic acid film fabrication method according to the first embodiment of the invention.

Although not shown in the drawings, the nucleic acid film 10 includes the coating layer 15 formed thereon such that the tip of the microneedle 11 is exposed. Here, the coating layer 15 may be formed on the nucleic acid film 10 by any one of the nucleic acid film fabrication methods set forth above.

In addition to the coating layer 15, the nucleic acid film 10 may further include the finishing layer 100 formed thereon. Here, the coating layer 15 and the finishing layer 100 may be formed on the nucleic acid film 10 by any one of the nucleic acid film fabrication methods set forth above.

With the coating layer 15, the strength of the microneedle 11 can be reinforced while the microneedle 11 can be prevented from being bent or broken.

The nucleic acid film-based drug administration device according to the fourth embodiment may further include a boundary film 20, a finishing film 30, and a decomposing liquid 50.

Since the boundary film 20, the finishing film 30, and the decomposing liquid 50 are the same as those of the drug administration device according to any one of the first to third embodiments, description thereof will be omitted.

According to the nucleic acid film fabrication methods and the nucleic acid film-based drug administration devices set forth above, the nucleic acid film 10 is applied to a transdermal delivery technology that relies on drug diffusion across the human skin, thereby improving penetration of the drug 40 into the skin while preventing skin problems. In addition, the microneedle 11, the buffer groove 12, and the drug delivery portion 13 having the drug injection hole 14 formed therethrough can be easily formed on the nucleic acid film 10 and the nucleic acid film 10 can have a uniform thickness.

Further, according to the present invention, it is possible to prevent intrusion of foreign matter into the nucleic acid film 10 while improving decomposition of the nucleic acid film 10. Moreover, the decomposing liquid 50 can be stably supplied to the nucleic acid film 10, thereby enabling stable delivery of the drug 40. Furthermore, depending on the form of delivery of the drug 40, the nucleic acid film can be patterned in various ways and the dosage of the drug 40 can be adjusted according to the pattern of the nucleic acid film.

In addition, according to the present invention, leakage of the drug 40 through the drug injection hole 14 and intrusion of foreign matter into the drug 40 can be prevented while protecting the nucleic acid film 10.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention.

| List of Reference numerals | |
|---|---|
| S1: mixing step | S2: stirring step |
| S3: mixed solution application step | S4: drying step |
| S5: surface treatment step | S6: mold preparation step |
| S7: film acquisition step | S8: oblique angle deposition step |
| S9: finishing application step | S10: finishing drying step |
| 1: mixing container | 1a: aqueous solution |
| 1b: nucleic acid | 2: stirring unit |
| 3: magnet | 4: sealant |
| 5: mold | 301: first mold |
| 302: second mold | 303: third mold |
| 311: needle groove | 312: buffer formation groove |
| 313: delivery groove | 314: injection protrusion |
| 6: surface treatment unit | 7: drying unit |
| 8: pipetting unit | 10: nucleic acid film |
| 100: finishing layer | |
| 11: microneedle | 12: buffer groove |
| 13: drug delivery portion | 14: drug injection hole |
| 15: coating layer | 15a: first deposition aid member |
| 20: boundary film | 30: finishing film |
| 31: perforation needle | 40: drug |
| 50: decomposing liquid | 60: protective film |
| 70: separation layer | |

What is claimed is:

1. A nucleic acid film-based drug administration device, comprising:
   a nucleic acid film consisting of a nucleic acid alone, the nucleic acid film configured to contact human skin;
   a finishing film stacked on the nucleic acid film; and
   a drug filling a first space between the nucleic acid film and the finishing film,
   wherein a microneedle or a drug delivery portion protrudes from one surface of the nucleic acid film towards the human skin.

2. The nucleic acid film-based drug administration device according to claim 1, further comprising:
   a boundary film stacked between the nucleic acid film and the finishing film; and
   a decomposing liquid filling a second space between the boundary film and the finishing film and comprising distilled water or deionized water,
   wherein the finishing film comprises a perforation needle protruding therefrom toward the boundary film and configured to perforate the boundary film, and the drug fills a third space between the nucleic acid film and the boundary film.

3. A nucleic acid film-based drug administration device comprising:
   a nucleic acid film consisting of a nucleic acid alone; and
   a drug, the nucleic acid film configured to contact human skin,
   wherein a microneedle or a drug delivery portion protrudes from one surface of the nucleic acid film towards the human skin.

4. The nucleic acid film-based drug administration device according to claim 3, further comprising:
   a boundary film stacked on the nucleic acid film;
   a finishing film stacked on the boundary film and comprising a perforation needle protruding therefrom toward the boundary film, the perforation needle being configured to perforate the boundary film; and
   a decomposing liquid filling a space between the boundary film and the finishing film and comprising distilled water or deionized water.

5. The nucleic acid film-based drug administration device according to claim 1, wherein a buffer groove is formed on other surface of the nucleic acid film to correspond to the microneedle or the drug delivery portion.

6. The nucleic acid film-based drug administration device according to claim 1, further comprising:
   a coating layer formed on the one surface of the nucleic acid film such that a tip of the microneedle or a tip of the drug delivery portion is exposed.

7. The nucleic acid film-based drug administration device according to claim 1, further comprising:
   a coating layer formed on the one surface of the nucleic acid film such that a portion of the coating layer corresponding to the microneedle or a portion of the coating layer corresponding to the drug delivery portion is open.

8. The nucleic acid film-based drug administration device according to claim 1, wherein the drug delivery portion has a drug injection hole formed therethrough to allow the drug to be discharged through the drug injection hole.

9. The nucleic acid film-based drug administration device according to claim 1, wherein a buffer groove is formed on other surface the nucleic acid film to correspond to the microneedle or the drug delivery portion.

10. The nucleic acid film-based drug administration device according to claim 9, further comprising:
    a coating layer formed on the other surface of the nucleic acid film such that a portion of the coating layer corresponding to the drug injection hole is open.

11. The nucleic acid film-based drug administration device according to claim 9, further comprising:
    a protective film detachably coupled to the one surface of the nucleic acid film such that the drug injection hole is open or closed.

* * * * *